United States Patent [19]

Beaver

[11] Patent Number: 5,004,848
[45] Date of Patent: Apr. 2, 1991

[54] METHOD OF ELEVATING THE MELTING POINT OF A HEXABROMOCYCLODODECANE PRODUCT

[75] Inventor: Phillip R. Beaver, Baton Rouge, La.

[73] Assignee: Ethyl Corporation, Richmond, Va.

[21] Appl. No.: 475,384

[22] Filed: Feb. 5, 1990

[51] Int. Cl.$^5$ .............................................. C07C 17/12
[52] U.S. Cl. .................................. 570/206; 570/190; 570/211
[58] Field of Search ............... 570/206, 207, 213, 190, 570/191, 196, 197, 208, 211

[56] References Cited

U.S. PATENT DOCUMENTS

| | | |
|---|---|---|
| 3,558,727 | 1/1971 | Jenkner et al. ........................ 570/206 |
| 3,652,688 | 3/1972 | Olechowski et al. ................ 570/206 |
| 3,833,675 | 9/1974 | Newcombe et al. ................. 570/206 |

FOREIGN PATENT DOCUMENTS

| | | |
|---|---|---|
| 3120621 | 5/1981 | Fed. Rep. of Germany . |
| 50-5187 | 2/1975 | Japan . |
| 2205830 | 12/1988 | United Kingdom ................ 570/206 |

Primary Examiner—Werren B. Lone
Attorney, Agent, or Firm—Terry B. Morris; David E. LaRose

[57] ABSTRACT

A method for producing high melting hexabromocyclododecane product by selective recovery of preferred isomers.

17 Claims, No Drawings

METHOD OF ELEVATING THE MELTING POINT OF A HEXABROMOCYCLODODECANE PRODUCT

BACKGROUND

This invention relates to the recovery of hexabromocyclododecane product, usable as flame retardant. In one aspect, this invention relates to methods for the recovery of a hexabromocyclododecane product having preferred ratios of isomers.

Bromination of cyclododecatriene produces hexabromocyclododecane isomers having differing melting points. The melting point characteristics of hexabromocyclododecane product obtained from these compositions are known to be related, in part, upon the ratios and distributions of hexabromocyclododecane isomers within the product. For instance, see U.K. Pat. Appl. 2,205,830 and Jap. Pat. Publ. (Kokoku) 50-5187. However, methods to provide an adjustment in the ratio of isomers to affect melting point characteristics are not taught and there continues to be a need for such methods.

The forming of an HBCD reaction mass by admixing bromine and cyclododecatriene in a solvent system comprising alcohol and halogenated hydrocarbon is illustrated in the following patents, incorporated in their entirety herein by reference:

U.S. Pat. No. 3,558,727 (Jenkner et al)
U.S. Pat. No. 3,652,688 (Olechowski et al)
U.S. Pat. No. 3,833,675 (Newcombe et al)
U.K. 2,205,830 (Hermolin et al)
D.E. 3,120,621 (Jenkner et al)

As illustrated in these patents, bromine and cyclododecatriene can be admixed in approximately stoichiometric amounts, optionally with a slight excess of bromine, e.g. about 3 to about 5 percent excess bromine, so as to permit bromination of the cyclododecatriene to form HBCD. This bromination occurs in a solvent system to effect the formation of the HBCD product. The final HBCD product formed by this reaction will typically comprise HBCD in solid particle form, these particle forms being tainted or contaminated with residual bromides (e.g. water soluble bromides such as halogen bromides) as well as unreacted or partially reacted cyclododecatriene (e.g. tetrabromocyclododecadene). The solvents of the solvent system can also react with one or more of the reactants to form possible contaminants, such as reaction with bromine to form alkyl bromides (e.g. isobutyl bromide when isobutyl alcohol is the alcohol in the solvent system). The method of admixing the reactants together with the solvent system can be varied, as illustrated in these patents, including as spacial introduction of the reactants apart from each other or the recycling of recovered mother liquor from downstream separation processes. Admixing can involve agitation of some sort so as to provide a more homogeneous reaction environment. The bromination of cyclododecatriene is an exothermic reaction which preferably can be controlled by cooling of the reaction mass to below about 70°. The prior art heretofore has shown a preference to cool to below 40° C.

SUMMARY

Improved methods have now been discovered for elevating the melting point of hexabromocyclododecane product obtained from a reaction mass formed by admixing bromine and cyclododecatriene in a solvent system comprising an alcohol and a halogenated hydrocarbon. These improved methods are effective in providing a ratio of hexabromocyclododecane isomers in the hexabromocyclododecane product so as to affect the melting point characteristics of such product.

DESCRIPTION OF THE PREFERRED EMBODIMENTS

Embodiments of the present invention consist of methods for elevating the melting point of an hexabromocyclododecane (hereinafter "HBCD") product obtained from a reaction mass formed by admixing bromine and cyclododecatriene in a solvent system comprising an alcohol and halogenated hydrocarbons. These improved methods comprise processing this composition to produce an HBCD product, this processing comprising separating the HBCD product particles according to size or to mass or to both size and mass, so as to preferentially retain higher melting point particles in the HBCD product.

Compositions formed by these and similar methods can contain a mixture of isomers of HBCD. At least three distinctive isomers can be discerned, each isomer having distinctive characteristics. These three isomers will be termed hereinafter as the "Alpha", "Beta", and "Gamma" isomers of HBCD. Unexpectedly, these three isomers have distinctive morphological, melting point and solvation characteristics such that compositions containing these isomers can be subjected to methods in accordance with embodiments of the present invention effective for elevating the melting point of the hexabromocyclododecane product.

Surprisingly, the Alpha and Beta isomers of HBCD have relatively lower melting points (i.e. below 185° C.) as compared to that (above 190° C.) of the Gamma isomer. The melting point range of the HBCD product is a function of the relative proportions of the isomers such that products with higher Gamma isomers have higher melting points. A further, unexpected distinctive characteristic of Alpha and Beta isomers produced by these methods are the relatively smaller size (dimensions) and mass (weight) of their formed particles compared to the Gamma isomer, which appears to agglomerate. An additional unexpected distinctive characteristic of these isomers is the temperature dependency of the solvation character such that the proportion of the isomeric particles in solution is a function of temperature.

Other embodiments of these improved methods comprise the steps of (1) maintaining the reaction mass
  (a) at a temperature of at least about 10° C to not more than about 70° C.,
  (b) at a loading factor of at least about 40 percent,
  (c) at a weight ratio of halogenated hydrocarbon/alcohol of from about 3/97 to about 90/10, at least until there is formed a composition comprising first particles predominant in a first HBCD isomer and second particles predominant in one or more other HBCD isomers, such first particles being larger in size and heavier in mass than the second particles and the first HBCD isomer having a higher melting point than each of the one or more other isomers; and (2) processing this formed composition to produce an HBCD product, this processing comprising separating the first and second particles according to size or to mass or to both size and mass so as to preferentially retain the first particles in the HBCD product.

In accordance with the embodiments of the present invention, a reaction mass is formed by the reaction of bromine and cyclododecatriene in a solvent system which is maintained at a temperature of at most about 70° C. and at a weight ratio of halogenated hydrocarbon to alcohol of about 3/97 to about 90/10. Maintenance of these conditions is sustained at least until there is formed a composition in accordance with the embodiments of the present invention, that is, a combination of HBCD particles containing Alpha, Beta and Gamma isomers. The initial temperature of the reaction mass when the reactants and solvents are admixed can be ambient temperature and the reaction mass can be allowed to rise in temperature through the exothermic reaction heat to a temperature of at least about 40° C. Once the temperature of the reaction mass reaches about 40° C., then cooling means can be effected to prevent the temperature from rising above 60° C. when ambient pressures are being utilized. Temperature can be permitted to rise above 60° by the use of pressurization, but the preferable temperature range is from at least about 40° C. to about 60° C., more preferably about 60° C.

The loading factor is the weight of theoretical HBCD product yield to the weight of the total reaction mass (including solvent). Low loading factors (e.g. below 40%) were favored in earlier methods to produce a high melting point HBCD product (e.g. initial melting point at about or above 190° C.). This was due to the belief that higher loading factors were counterproductive in attaining HBCD products with relatively higher initial melting points due to higher proportionation favoring of the Alpha and Beta isomers. Applicant's improved methods now make possible the attainment of high melting point HBCD products from compositions produced from reaction masses having higher loading factors. Those higher loading factors can be used in either batch or continuous reaction processes, including also processes with recycling of at least a portion of the product from downstream of the reaction.

The solvent system for the reaction mass comprises an admixture of certain halogenated hydrocarbons and alcohols, which halogenated hydrocarbons and alcohols can be those used typically in the bromination of cyclododecatriene to form HBCD. Illustrative of such halogenated hydrocarbon and alcohols are found in U.S. Pat. No. 3,833,675; U.S. Pat. No. 3,652,688 and U.S. Pat. No. 3,558,727. These solvents are preferably lower alkyl alcohols and lower alkyl halogenated hydrocarbons (the term "lower alkyl" as used herein means $C_1$-$C_6$ linear or branched alkyl groups). The preferred solvents are $C_1$-$C_4$ alcohols and $C_1$-$C_4$ alkyl halides, the halides having one or more halogens in which the halogen is bromine, chlorine or both bromine and chlorine as substituents on the same alkyl group but not necessarily the same carbon atom. Most preferably, the solvents used in embodiments of the present invention include t-butyl alcohol, ethanol, n-propanol, isopropanol, n-butanol, methanol, 2-methylpropanol-1, butanol-2, carbon tetrachloride, chloroform, and dibromomethane. Most preferred is a solvent system comprising isobutyl alcohol and chloroform or isobutyl bromide. The weight ratio of halogenated hydrocarbon to alcohol ranges from about 3/97 to about 90/10. Preferably the weight ratio of halogenated hydrocarbon to alcohol is at least about 85/15 to about 95/5.

Three variables (i.e. temperature, loading factor and weight ratio) are maintained at least until there is formed a composition comprising first particles predominant in a first HBCD isomer and second particles of one or more other HBCD isomers. The first particle, predominant in a first HBCD isomer, can be tainted or contaminated with residual bromides (e.g. hydrogen bromide) and solvents, but preferably is not so tainted or contaminated. The first HBCD isomer contained within these first particles is one which has a higher melting point than the other isomers formed in the reaction. Preferably this first HBCD isomer will have a melting point of at least about 195° C. The second particles comprise the other HBCD isomers formed by the reaction performed in accordance with the process of the present invention. These second particles individually can comprise predominantly only one of the other isomers or combinations thereof and likewise can be tainted or contaminated as the first particles. Both first and second particles can comprise HBCD isomers other than the predominant isomer, but not in significant amounts. By maintaining the reaction mass in accordance with embodiments of the present invention, the first particles are larger in size and heavier in mass than the second particles. Without wishing to be bound by theory, it is believed that these first particles are larger in size because of an agglomeration effect which occurs by maintaining the reaction mass in accordance with the embodiments of the present invention. Once the start of formation of first particles has been effected, the amount formed is generally a function of time and continues until completion of the reaction, generally from 30 minutes to about three hours in a batch reaction.

The composition can then be processed to produce the desired HBCD product. In such processing, typically the reaction mass is permitted to cool to ambient temperature. Cooling can be done with an induced cooling rate of about 45° C. per minute. Preferably, cooling to a temperature of no more than about 40° C. The reaction mass can then be subjected to typical separation techniques (e.g. filtration, centrifugation or decantation) to recover the solid particles from the reaction mass. Such separations in accordance with the embodiments of the invention can effect a preferential recovery of the higher melting point particles by utilizing the differences existing in the size and mass of the first particles and of the second particles. Washing of the separated HBCD particles can be effected by the techniques known to those in the art. Illustrative of these methods include rinsing filtrate on a filter. Alternatively, separated particles can be slurried in a solvent or water and subsequently filtered. Additional benefit (i.e. increased first particle content and elevated melting point) results by the use of a cool (e.g. about 0° C. to about 30° C.) solvent rinse or wash of the particles due to a preferential dissolving of one or more of the lower melting HBCD isomers as a function of wash temperature. Alternatively, sequential separating and rinsing or washing can be performed and/or repeated in various sequences. Separating can be performed by methods such as centrifuging or filtering, preferably using true running filtering (i.e. once through treatment without recycling).

The HBCD product obtained by the process of the present invention preferably comprise at least 90 percent by weight, more preferably at least 95 percent by weight, of the first particles. This preferred HBCD product more preferably has a melting point of at least about 195° C.

The following examples illustrate one or more embodiments of the invention, but are not intended to limit the invention to a particular set of parameters.

Experiment 1

A reaction mass was produced by admixing cyclododecatriene and bromine (approximately 1 mole cyclododecatriene to 3 moles bromine plus about one weight percent bromine in excess) in a solvent solution of chloroform and isobutyl alcohol (36.5 and 63.5 weight percent respectively) with a loading factor of 52 percent (weight of theoretical reaction product/total reaction mass including solvent weight). Reaction was for 12 hours and at 30° C. with agitation (50 rpm). Neutralization with an approximately stoichiometric amount of $Na_2CO_3$ was performed at 36° C. with agitation (40 rpm). A product yield of 84.1 percent was obtained. A sample (Sample 1-a) was drawn and analysis of the hexabromocyclododecane isomer distribution was made. The results are reported in Table A hereinbelow. The reaction mass was then subjected to centrifugation with recycling of filtrate until clear filtrate was obtained. Analysis of the hexabromocyclododecane isomer distribution at ¼ inch from the cake top (Sample 1-b) and 2 inches from the cake top (Sample 1-c) were performed and is reported below in Table A.

Experiment 2

A sample was drawn from the reaction mass of Experiment 1 after neutralization and before centrifugation. This mass was allowed to stand undisturbed for 30 minutes, producing stratification into three layers: Layer 1 being predominantly clear liquor, Layer 2 being flocculation and Layer 3 being settled crystals. Samples 2-a, 2-b, and 2-c were drawn from Layers 1, 2 and 3 respectively and analyzed by high performance liquid chromatography for hexabromocyclododecane isomer distribution. The results are tabulated in Table A hereinbelow.

TABLE A

| Sample | Alpha % | Beta % | Gamma % |
|---|---|---|---|
| 1-a (reaction mass) | 10.5 | 6.9 | 80.2 |
| 1-b (¼ inch - centrifugation) | 21.5 | 25.6 | 49.8 |
| 1-c (2 inch - centrifugation) | 9.4 | 4.6 | 84.1 |
| 2-a (Layer 1) | 18.6 | 26.5 | 9.3 |
| 2-b (Layer 2) | 13.6 | 31.3 | 46.9 |
| 2-c (Layer 3) | 8.3 | 4.4 | 84.3 |

What is claimed is:

1. A method for elevating the melting point of hexabromocyclododecane product obtained from a reaction mass formed by admixing bromine and cyclododecatriene in a solvent system comprising the admixture of a lower alkyl alcohol and a lower alkyl halogenated hydrocarbon, said method comprising the steps of:
   (1) maintaining said reaction mass
      (a) at a temperature of at least about 40° C.,
      (b) at a loading factor of at least about 40%, and
      (c) at a weight ratio of said halogenated hydrocarbon to said alcohol of about 3/97 to about 90/10,
   at least until there is formed a composition comprising first particles predominant in a first hexabromocyclododecane isomer and second particles of one or more other hexabromocyclododecane isomers, said first particles being larger in size and heavier in mass than said second particles and said first isomer having a higher melting point than each of said one or more other isomers; and
   (2) processing said composition to produce said HBCD product, said processing comprises separating said first and second particles according to size or mass so as to preferentially retain said first particles in said hexabromocyclododecane product.

2. The method of claim 1 wherein said first HBCD isomer has a melting point of at least about 185° C.

3. The method of claim 2 wherein said HBCD product comprises at least about 95% by weight of said first particles.

4. The method of claim 1 wherein said temperature is about 60° C.

5. The method of claim 1 wherein said halogenated hydrocarbon is chloroform.

6. The method of claim 5 wherein said alcohol is isobutyl alcohol.

7. The method of claim 1 wherein said weight ratio of halogenated hydrocarbon to alcohol is at least about 85/15.

8. The method of claim 1 wherein said composition is cooled to at no more than about 40° C. prior to said separating.

9. The method of claim 1 wherein at least a portion of said second particles are dissolved by wash solvent prior to or contemporaneous with said separating.

10. The method of claim 9 wherein said wash solvent has a temperature of about 0° C. to about 30° C.

11. The method of claim 1 wherein said separating is either centrifuging or filtering.

12. The method of claim 11 wherein said filtering is true running filtering.

13. The method of claim 1 comprising the step of rapidly cooling the composition formed in step 1 before processing the composition of step 2.

14. The method of claim 13 wherein cooling is performed at a cooling rate of at least 45° C. per minute.

15. The method of claim 1 wherein step 2 comprise cool solvent rinsing or washing of first and second particles.

16. The method of claim 15 wherein said cool solvent has a temperature of about 0° C. to about 30° C.

17. A method of producing hexabromocyclododecane product from a composition comprising a first hexabromocyclododecane isomer solid and one or more other hexabromocyclododecane isomer solids, said first isomer solid being characterized by a relatively higher melting point range than that of each of said one or more other isomer solids,
   said method comprising effectively separating said first isomer solids from one or more other isomer solids to produce a product comprising at least about 95% by weight of said first isomer solid.

* * * * *

UNITED STATES PATENT AND TRADEMARK OFFICE
CERTIFICATE OF CORRECTION

PATENT NO. : 5,004,848
DATED : April 2, 1991
INVENTOR(S) : Phillip R. Beaver

It is certified that error appears in the above-identified patent and that said Letters Patent is hereby corrected as shown below:

Column 6, line 44 reads "of step 2" and should read -- in step 2 --.

Column 6, line 46 reads "at least 45°C" and should read -- at least about 45°C --.

Signed and Sealed this

First Day of December, 1992

Attest:

DOUGLAS B. COMER

Attesting Officer

Acting Commissioner of Patents and Trademarks